US007769218B2

(12) United States Patent
Crucs (10) Patent No.: US 7,769,218 B2
(45) Date of Patent: Aug. 3, 2010

(54) SYSTEM AND METHOD TO ADJUST MEDICAL IMAGING EQUIPMENT (75) Inventor: Kevin M. Crucs, Akron, OH (US)

(73) Assignee: Apteryx, Inc., Akron, OH (US)

( * ) Notice: Subject to any disclaimer, the term of this patent is extended or adjusted under 35 U.S.C. 154(b) by 1112 days.

(21) Appl. No.: 11/244,545

(22) Filed: Oct. 6, 2005

(65) Prior Publication Data

US 2006/0213996 A1      Sep. 28, 2006

Related U.S. Application Data (60) Provisional application No. 60/664,448, filed on Mar. 23, 2005.

(51) Int. Cl.
*G06K 9/00* (2006.01)

(52) U.S. Cl. .................. 382/132; 382/128; 382/115

(58) Field of Classification Search ............. 382/100, 382/115–118, 128, 131–132
See application file for complete search history.

(56) References Cited

U.S. PATENT DOCUMENTS

| 5,469,353 | A | 11/1995 | Pinsky et al. |
| 5,592,374 | A | 1/1997 | Fellegara et al. |
| 6,247,813 | B1 * | 6/2001 | Kim et al. ................. 351/206 |
| 6,287,257 | B1 | 9/2001 | Matichuk |
| 6,826,554 | B2 * | 11/2004 | Sone ........................... 707/2 |
| 7,003,070 | B1 * | 2/2006 | Chen et al. .................. 378/17 |
| 7,149,325 | B2 * | 12/2006 | Pavlidis et al. ............ 382/103 |

OTHER PUBLICATIONS

International Search Report for PCT/US06/33385 mailed Jun. 4, 2007.

* cited by examiner

*Primary Examiner*—Wes Tucker
(74) *Attorney, Agent, or Firm*—Hahn Loeser & Parks LLP (57) ABSTRACT A system and method for automatically adjusting parameters of an imaging machine are disclosed. The system comprises a storage device for storing demographic information of at least one person to be imaged. The system also includes a computerized platform to retrieve the demographic information from the storage deviced and to generate adjustment data based on the demographic data for a next person to be imaged. The system further includes an imaging machine to receive the adjustment data from the computer and to adjust at least one parameter of the imaging machine in response to the adjustment data.

22 Claims, 6 Drawing Sheets

SYSTEM AND METHOD TO ADJUST MEDICAL IMAGING EQUIPMENT

CROSS-REFERENCE TO RELATED APPLICATIONS/INCORPORATION BY REFERENCE

This patent application claims priority to and the benefit of U.S. Provisional Patent Application Ser. No. 60/664,448 which was filed on Mar. 23, 2005, and is incorporated herein by reference in its entirety.

TECHNICAL FIELD

Certain embodiments of the present invention relate to medical imaging equipment. More particularly, certain embodiments of the present invention relate to a system and method to automatically adjust certain parameters of medical imaging equipment such as, for example, a height of a sensor.

BACKGROUND OF THE INVENTION

The military often needs to take medical images of new recruits as part of their entrance process. For example, pan-tomograph X-ray images of each recruit's head may need to be taken to have an accurate dental record of each recruit. In capturing a pan-tomograph image, a sensor of the imaging machine is rotated around the recruit's head. The military typically has to deal with many recruits at one time. It, is typical for the recruits to be lined up according to height and to image one recruit after another. However, as the height of each recruit may be different, the imaging sensor of the imaging machine may need to be manually adjusted by, for example, an X-ray technician to correspond to the height of the next person (i.e., recruit) to be imaged. Such manual adjustments are time consuming and, after imaging many recruits (perhaps thousands), much time is wasted that could be used by the X-ray technician to accomplish other tasks.

Also, an X-ray dosage and time duration of exposure may need to be adjusted for each recruit to be imaged as well. For example, a higher X-ray dosage may need to be set for a next recruit to be imaged, who weighs more, than for a recruit that has just been imaged. Having to manually adjust an X-ray dosage for each recruit can also result in much wasted time. Other parameters of the imaging machine may have to be manually adjusted as well for different recruits.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

A first embodiment of the present invention provides a method for automatically adjusting an imaging machine. The method comprises retrieving demographic data of a next person to be imaged from a storage device using a processor-based platform and generating adjustment data based on the demographic data using the processor-based platform. The method further comprises sending the adjustment data from the processor-based platform to an imaging machine to be used to image at least a portion of the next person. The method also comprises adjusting at least one parameter of the imaging machine in response to the adjustment data and imaging at least a portion of the next person with the imaging machine after adjusting the at least one parameter.

Another embodiment of the present invention comprises a system for automatically adjusting parameters of an imaging machine. The system includes a storage device for storing demographic information of at least one person to be imaged. The system also includes a computerized device to retrieve the demographic information from the storage device and to generate adjustment data based on the demographic data for a next person to be imaged. The system further includes an imaging machine to receive the adjustment data from the computerized device and to adjust at least one parameter of the imaging machine in response to the adjustment data.

A further embodiment of the present invention comprises a method for automatically adjusting a medical imaging machine. The method comprises capturing sensed characteristic information from a next person to be medically imaged using a sensor device (e.g., a transmitter and a receiver) and transmitting the sensed characteristic information from the sensor device to a processor-based platform. The method further comprises generating adjustment data based on the sensed characteristic information using the processor-based platform and sending the adjustment data from the processor-based platform to a medical imaging machine to be used to medically image at least a portion of the next person. The method also includes adjusting at least one parameter of the medical imaging machine in response to the adjustment data and imaging at least a portion of the next person with the medical imaging machine after adjusting the at least one parameter.

Another embodiment of the present invention comprises a system for automatically adjusting parameters of a medical imaging machine. The system includes a sensor device to capture sensed characteristic information of a next person to be medically imaged. The system further includes a computer to receive the sensed characteristic information from the sensor device and to generate adjustment data based on the sensed characteristic information. The system also includes a medical imaging machine to receive the adjustment data from the computer and to adjust at least one parameter of the medical imaging machine in response to the adjustment data.

These and other advantages and novel features of the present invention, as well as details of an illustrated embodiment thereof, will be more fully understood from the following description and drawings.

DETAILED DESCRIPTION OF THE INVENTION

For purposes of describing embodiments of the present invention, the following definitions are to be used and, if necessary, supercede any commonly understood definition of the terms.

demographic data/information—any apriori data or information that relates to certain features of a person such as, for example, height, weight, age, sex, pregnancy status.

sensed characteristic information—sensed data that captures features of a person such as, for example, a calibrated photographic image that allows a person's height to be ascertained, or a person's weight or mass.

adjustment data—data that may be used by an imaging machine to adjust at least one parameter of the imaging machine such as, for example, a height position of an X-ray sensor of the imaging machine or an X-ray dosage amount of the imaging machine.

Figure 1A:
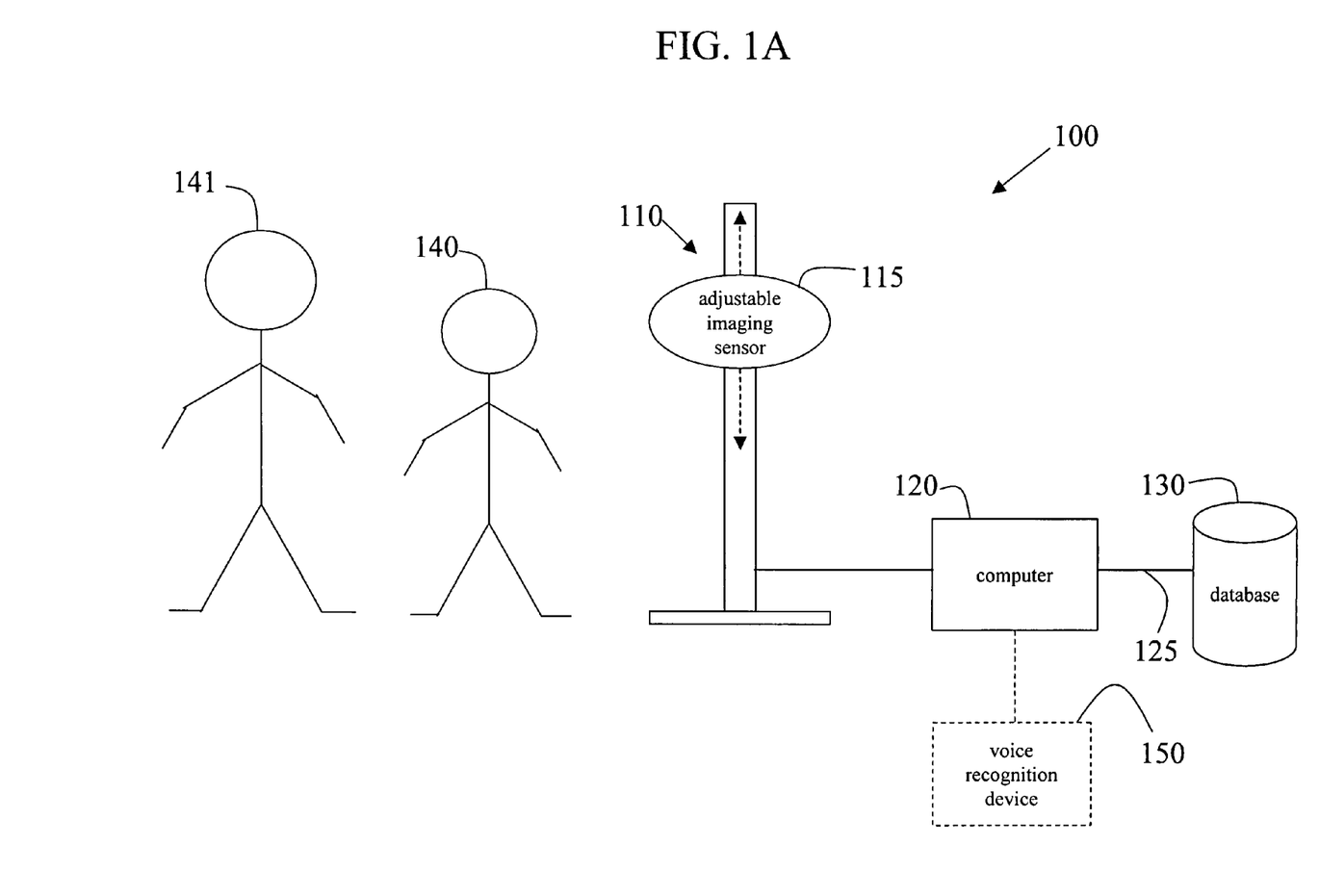
FIG. 1A is a schematic diagram of a first exemplary embodiment of a system for automatically adjusting parameters of an imaging machine, in accordance with various aspects of the present invention.

FIG. 1A is a schematic diagram of a first exemplary embodiment of a system 100 for automatically adjusting parameters of an imaging machine 110, in accordance with various aspects of the present invention. The system 100 comprises an imaging machine 110, a computer 120, and a storage device 130 such as a server hosting a database. The computer 120 interfaces to both the storage device 130 and the imaging machine 110 via standard digital communication interfaces (wired or wireless). The imaging machine 110 includes a re-positionable imaging sensor 115 (e.g., a medical transmitter/receiver). For example, the imaging sensor 115 may be moved up and down, depending on the height of a next person 140 to be imaged.

In accordance with various embodiments of the present invention, the imaging machine 110 may comprise an X-ray imaging machine for taking pan-tomograph images of people, or any other type of medical imaging machine that is used to image at least one portion of a person's body (e.g., ultrasound, X-ray, magnetic resonance, computed tomography (CT), etc.).

In accordance with various embodiments of the present invention, the computer 120 may be a personal computer (PC), a work station, or any other processor-based platform or computerized device that may be used to accomplish the functions of the computer 120 as described herein. The computer 120 may be a standalone platform or may be an integral part of the imaging machine 110, in accordance with various embodiments of the present invention.

The storage device 130 may be a server, a hard drive on a PC, a dedicated memory, a database, an imaging sensor such as, for example, a camera, or any other type of digital storage device that may be used to accomplish the functions of the storage device 130 as described herein, in accordance with various embodiments of the present invention. The storage device 130 may be a standalone device or may be an integral part of the computer 120 or imaging machine 110, in accordance with various embodiments of the present invention.

If the storage device 130 is a standalone device, the connection 125 between the computer 120 and the storage device 130 may be a network connection such that the storage device may be remotely located from the computer 120 and imaging machine 110. The storage device 130 may be part of a DICOM compatible system, a patient list, or a practice management application, for example. A database application hosted on the storage device 130 is used to manage the demographic data. The demographic data may include, for example, a height, a weight, an age, and/or a sex of at least one person to be medically imaged. Other demographic data are possible as well.

Figure 2:
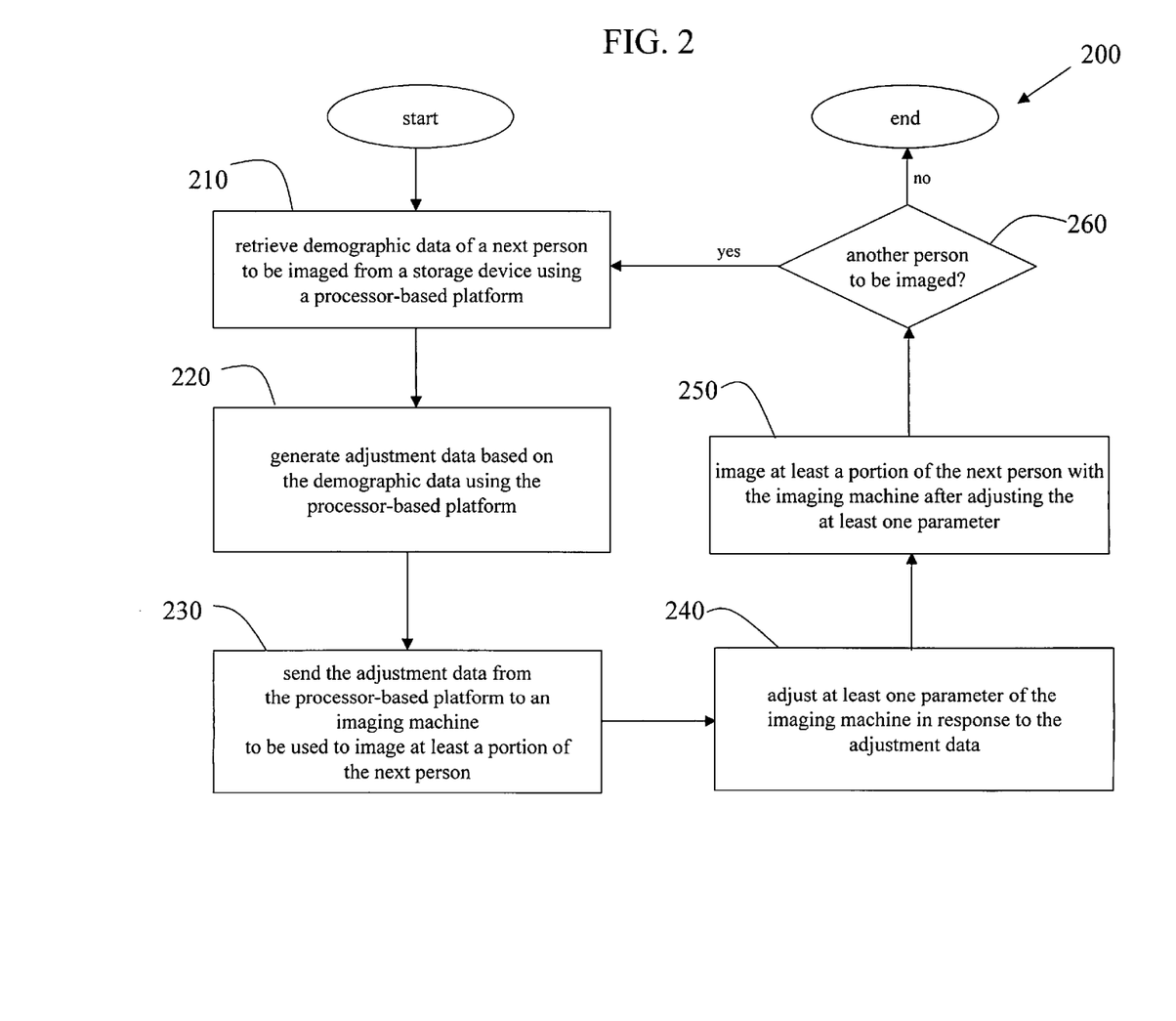
FIG. 2 is a flowchart of a first exemplary embodiment of a method for automatically adjusting an imaging machine using the system of FIG. 1 or FIG. 2, in accordance with various aspects of the present invention.

FIG. 2 is a flowchart of a first exemplary embodiment of a method 200 for automatically adjusting an imaging machine 110 using the system 100 of FIG. 1, in accordance with various aspects of the present invention. In step 210, demographic data of a next person 140 to be imaged is retrieved from a storage device using a processor-based platform. For example, the computer 120 (i.e., processor-based platform) may read height and weight information that was previously stored (i.e., apriori data) in the database of the storage device 130 for the next person 140 to be imaged. In step 220, adjustment data is generated based on the demographic data using the processor-based platform. For example, the height demographic data may be used by the computer 120 to generate a first adjustment data which will tell the imaging machine 110 how to position a height of the imaging sensor 115. Also, the height and weight demographic data may be used by the computer 120 to generate a second adjustment data which will tell the imaging machine 110 how to set an X-ray dosage amount to be delivered by the imaging machine 110 and a time duration of exposure.

In step 230, the adjustment data is sent from the processor-based platform 120 to an imaging machine 110 to be used to image at least a portion of the next person 140. For example, the first and second adjustment data may be sent by the computer 120 to the imaging machine 110. In step 240, at least one parameter of the imaging machine 110 is automatically adjusted in response to the adjustment data. For example, the first and second adjustment data may be used by the imaging machine 110 to adjust a height position of the imaging sensor 115 and the X-ray dosage amount to be delivered by the imaging machine 110.

In step 250, at least a portion of the next person 140 to be imaged is imaged with the imaging machine 110 using the adjusted parameters accomplished in step 240. For example, the person 140 stands at a pre-determined position with respect to the imaging machine 110. The imaging sensor 115 is already positioned correctly to take a pan-tomograph image of the person's head and the X-ray dosage is already set to account for the fact that the person 140 is significantly overweight for his height. In step 260, a decision is made as to whether or not there is another person 141 to be subsequently imaged. If so, the method starts again at step 210, otherwise, the method ends.

In accordance with an embodiment of the present invention, the computer 120 knows the identity of the next person to be imaged 141 because the names of the persons to be imaged are retrieved alphabetically by the computer 120 and the persons to be imaged are lined-up in alphabetical order. Other pre-defined orders are possible as well. Alternatively, a next person to be imaged (or an operator of the system 100) may speak the name or identification number of the next person to be imaged into a voice recognition device 150 which interfaces to the computer 120. As a result, the computer 120 knows which corresponding demographic information to retrieve from the database.

Figure 1B:
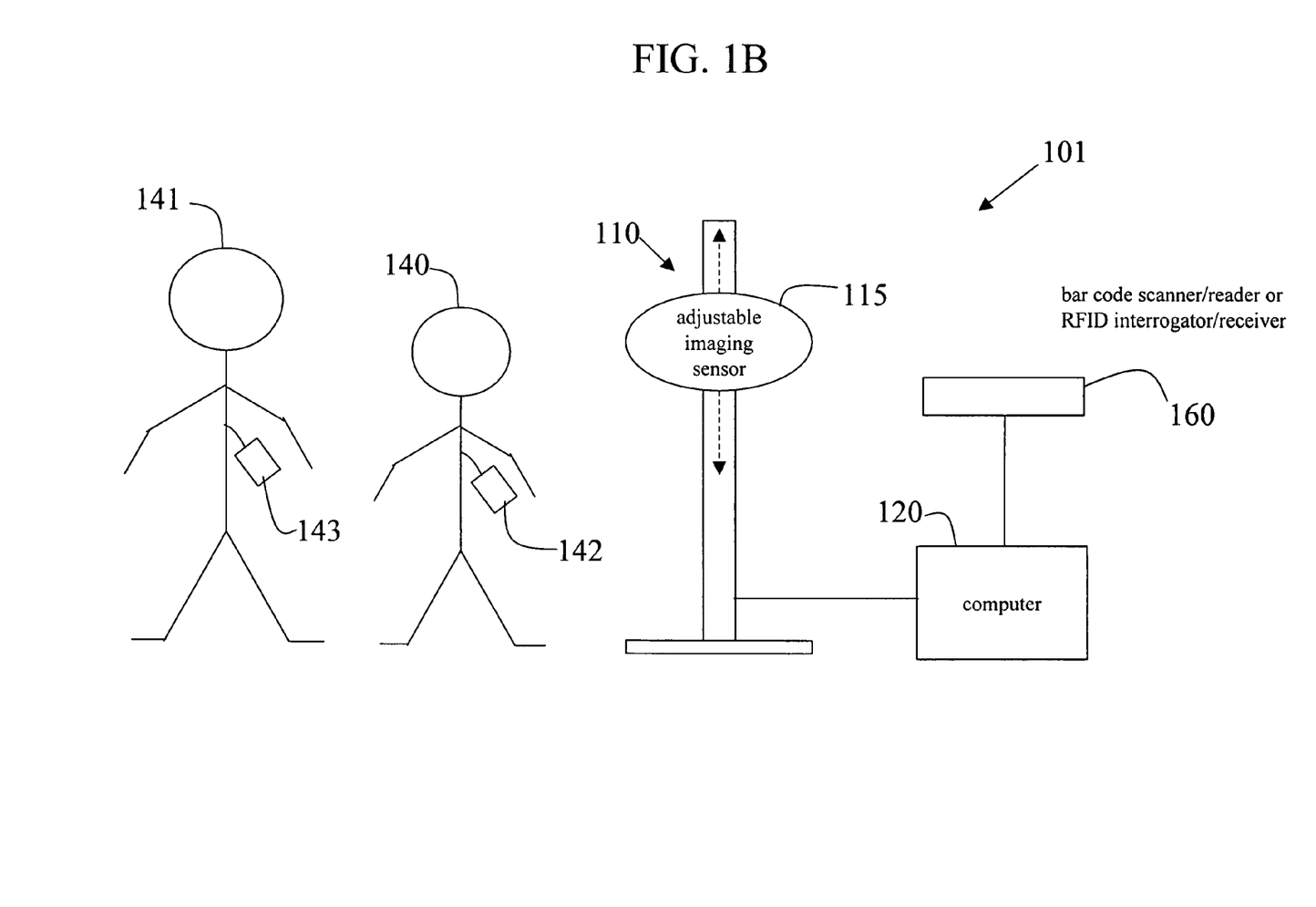
FIG. 1B is a schematic diagram of a second exemplary embodiment of a system for automatically adjusting parameters of an imaging machine, in accordance with various aspects of the present invention.

FIG. 1B is a schematic diagram of a second exemplary embodiment of a system 101 for automatically adjusting parameters of an imaging machine 110, in accordance with various aspects of the present invention. The system 101 comprises an imaging machine 110, a computer 120, a storage device 142 and/or 143 (e.g., RF ID tags or bar code badges), and scanner/reader 160 (e.g., a bar code scanner/reader or an RFID interrogator/receiver). The computer 120 interfaces to both the scanner/reader 160 and the imaging machine 110 via standard digital communication interfaces (wired or wireless). The imaging machine 110 includes a re-positionable imaging sensor 115. For example, the imaging sensor 115 may be moved up and down, depending on the height of a next person 140 to be imaged.

In accordance with various embodiments of the present invention, the imaging machine 110 may comprise an X-ray imaging machine for taking pan-tomograph images of people, or any other type of medical imaging machine that is used to image at least one portion of a person's body (e.g., ultrasound, X-ray, magnetic resonance, computed tomography (CT), etc.).

In accordance with various embodiments of the present invention, the computer 120 may be a personal computer (PC), a work station, or any other processor-based platform that may be used to accomplish the functions of the computer 120 as described herein. The computer 120 may be a standalone platform or may be an integral part of the imaging machine 110, in accordance with various embodiments of the present invention. In accordance with various embodiments of the present invention, the computer 120, the scanner/reader 160, or the combination thereof may be referred to as a computerized device.

The storage devices 142 and 143 may be RF ID tags worn by the persons to be imaged or badges with a bar code worn by the persons to be imaged. Each RF ID tag and bar code badge contains the demographic information of the person the tag or badge belongs to. The demographic data may include, for example, a height, a weight, an age, and/or a sex of at least one person to be medically imaged. Other demographic data are possible as well. In the case of an RF ID tag, the scanner/reader 160 is an RFID interrogator/receiver which interrogates the RF ID tag 142 of the next person to be imaged and receives back the corresponding demographic information. In the case of a bar code badge, the scanner/reader 160 is a bar code scanner/reader which scans a bar code on the bar code badge 142 and reads the demographic information encoded in the bar code. In either case, the demographic information is sent to the computer 120 where adjustment data is generated in response to the demographic data. Then, a parameter of the imaging machine 110 is adjusted in response to the adjustment parameters as described previously.

As an alternative, the RF ID tag and the bar code of the bar code badge, 142 or 143, may encode only an identification number of the corresponding person to be imaged. In such a case, the identification number would be read by the scanner/reader 160 and forwarded to the computer 120. The actual demographic information may be stored on the computer 120 or, for example, in a database 130 on a server. The identification number is used to retrieve the corresponding demographic information for the next person to be imaged.

Figure 3:
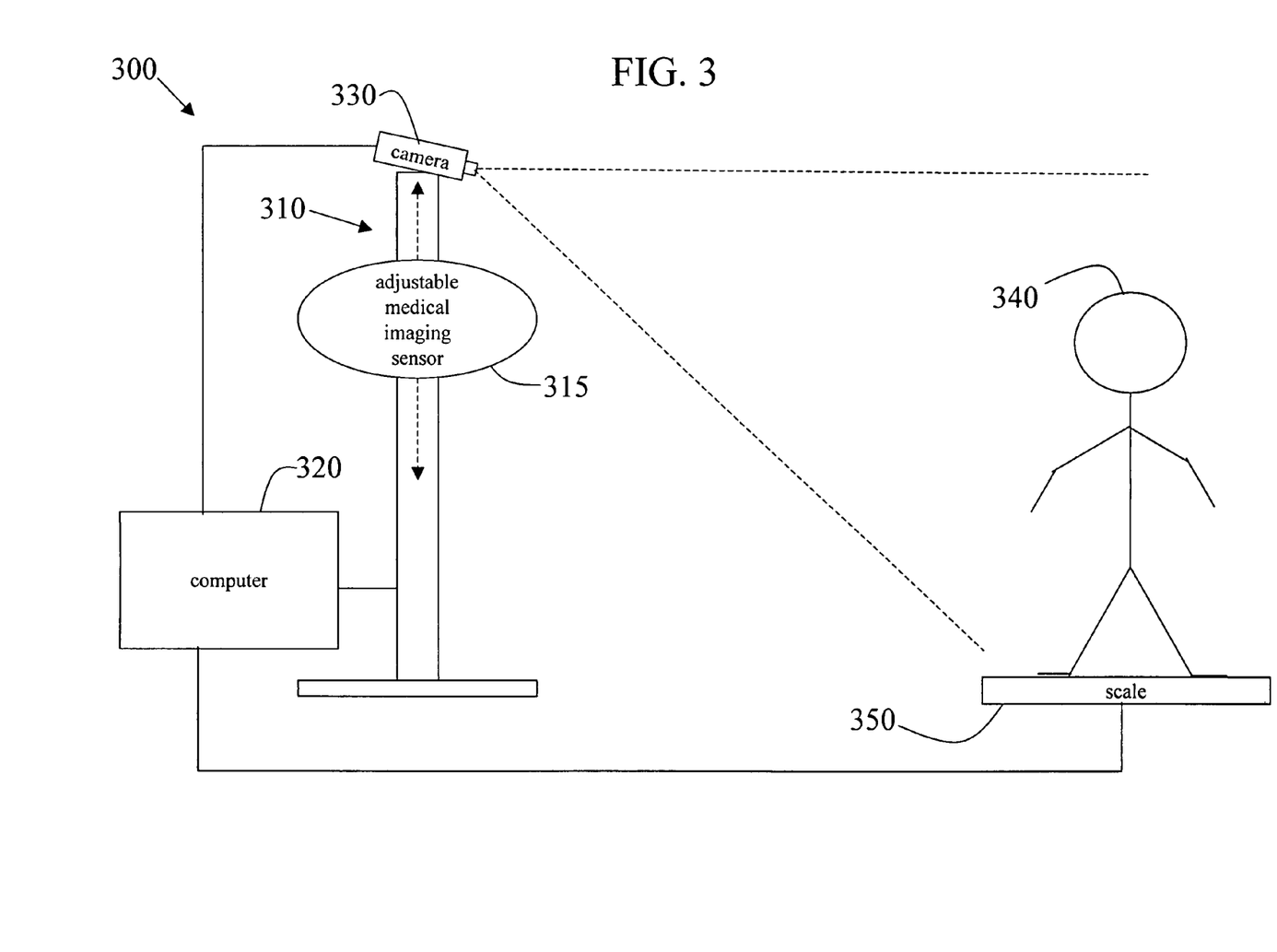
FIG. 3 is a schematic diagram of a third exemplary embodiment of a system for automatically adjusting parameters of an imaging machine, in accordance with various aspects of the present invention.

FIG. 3 is a schematic diagram of a third exemplary embodiment of a system 300 for automatically adjusting parameters of an imaging machine 310, in accordance with various aspects of the present invention. The system 300 comprises an imaging machine 310, a computer 320, a sensor device 330 (e.g., a digital camera), and a scale 350. The computer 320 interfaces to the sensor device 330, the imaging machine 310, and the scale 350 via standard digital communication interfaces (wired or wireless). The imaging machine 310 includes a re-positionable imaging sensor 315. For example, the imaging sensor 315 may be moved up and down, depending on the height of a person 340 to be imaged.

In accordance with various embodiments of the present invention, the imaging machine 310 may comprise an X-ray imaging machine for taking pan-tomograph images of people, or any other type of medical imaging machine that is used to image at least one portion of a person's body (e.g., ultrasound, X-ray, magnetic resonance, computed tomography, etc.).

In accordance with various embodiments of the present invention, the computer 320 may be a personal computer (PC), a work station, or any other processor-based platform that may be used to accomplish the functions of the computer 320 as described herein. The computer 320 may be a standalone platform or may be an integral part of the imaging machine 310 or the sensor device 330, in accordance with various embodiments of the present invention.

The sensor device 330 may be, for example, a calibrated digital camera or any other type of sensor device or biometric device that is capable of sensing and measuring at least one characteristic of the person to be imaged 340 (e.g., a laser device to measure a height of the person 340). The sensor device 330 may be a standalone device or may be an integral part of the imaging machine 310 and/or the computer 320, for example. The scale 350 may be a standard electronic scale that outputs a weight measurement when a person stands on the scale. The weight measurement data is electronically communicated (wired or wirelessly) to the computer 320.

Figure 4:
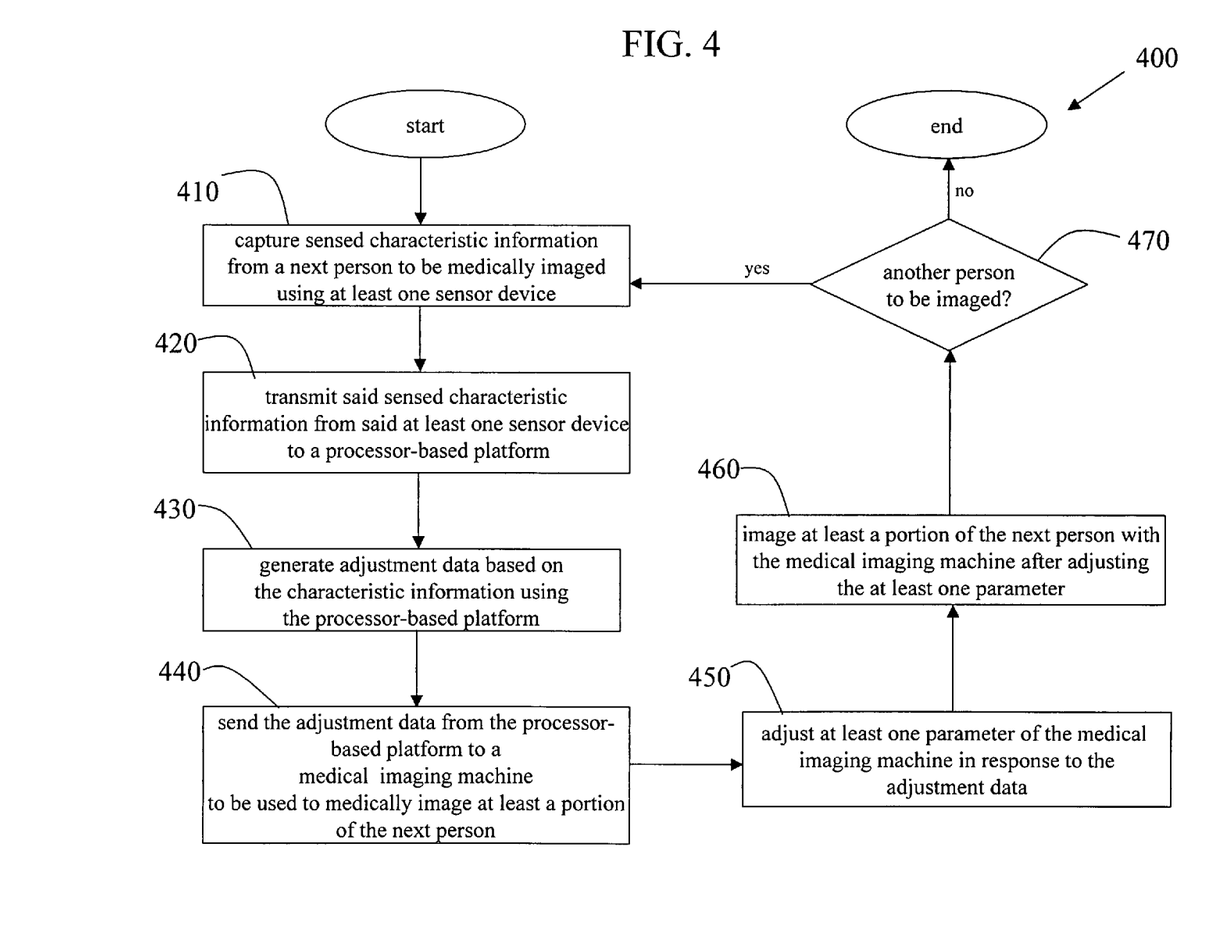
FIG. 4 is a flowchart of a second exemplary embodiment of a method for automatically adjusting an imaging machine using the system of FIG. 3, in accordance with various aspects of the present invention.

FIG. 4 is a flowchart of a second exemplary embodiment of a method 400 for automatically adjusting an imaging machine 310 using the system 300 of FIG. 3, in accordance with various aspects of the present invention. In step 410, sensed characteristic information is captured from a next person to be medically imaged using at least one sensor device. For example, the camera 330 may capture a calibrated digital image (i.e., sensed characteristic information) of the next person to be medically imaged 340, or the scale 350 may capture a weight or mass measurement (i.e., sensed characteristic information) of the next person to be medically imaged 340. In step 420, the sensed characteristic information is transmitted from the at least one sensor device to a processor-based platform. For example, the calibrated digital image and the measured weight may be transmitted to the computer 320 in step 420.

The computer 320 may analyze the sensed characteristic data (e.g., the calibrated digital image) and ascertain the height of the next person 340 to be medically imaged. In step 430, adjustment data is generated based on the sensed characteristic information using the processor-based platform 320. For example, the computer 320 may take the height information of the person 340 and generate position data for the imaging sensor 315. Also, the computer 320 may take the weight information of the person 340 and generate a transmit dosage amount (e.g., an X-ray dosage amount) for the imaging sensor 315.

In step 440, the adjustment data is sent to a medical imaging machine 310 to be used to medically image the next person 340. For example, the position data for the imaging sensor 315 may be sent from the computer 320 to the medical imaging machine 310. In step 450, at least one parameter of the medical imaging machine 310 is adjusted in response to the adjustment data. For example, the imaging sensor 315 is driven from a first position to a second position where the second position corresponds to a height of the next person 340 to be imaged.

In step 460, the next person 340 to be imaged is imaged with the medical imaging machine 310 using the adjusted parameters accomplished in step 450. For example, the person 340 stands at a pre-determined position with respect to the imaging machine 310. The imaging sensor 315 is already positioned correctly to take a pan-tomograph image of the person's head. In step 470, a decision is made as to whether or not there is another person to be subsequently imaged. If so, the method starts again at step 410, otherwise, the method ends.

Figure 5:
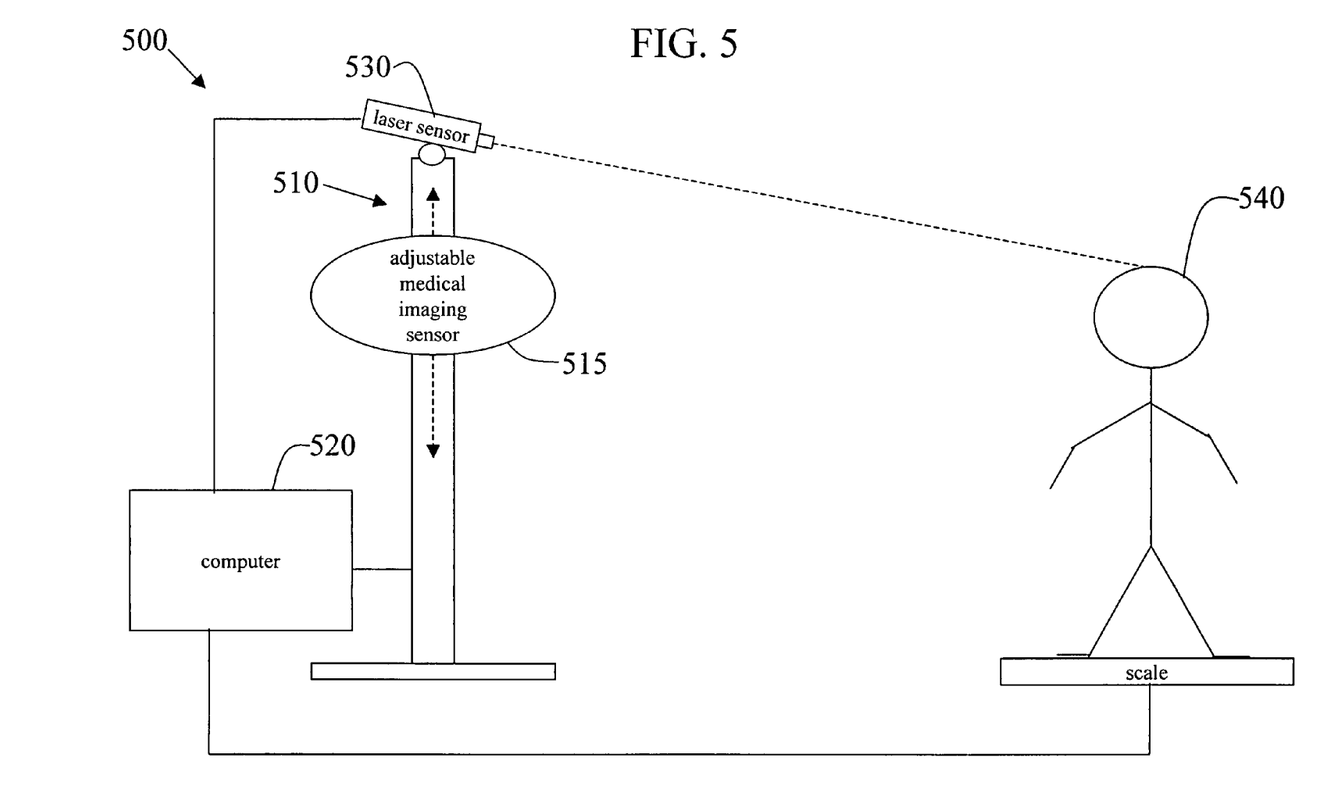
FIG. 5 is a schematic diagram of a fourth exemplary embodiment of a system for automatically adjusting parameters of an imaging machine, in accordance with various aspects of the present invention.

FIG. 5 is a schematic diagram of a fourth exemplary embodiment of a system 500 for automatically adjusting parameters of an imaging machine 510, in accordance with various aspects of the present invention. The system 500 of FIG. 5 is very similar to the system 300 of FIG. 3 except that, in FIG. 5, the sensor device 530 is a laser sensor which is used to measure the height of the next person to be imaged 540. The laser sensor sends height information to the computer 520 such that the adjustable medical imaging sensor 515 may be adjusted to an appropriate height for the next person 540 to be medically imaged.

In summary, embodiments of the present invention provide a system and method for automatically adjusting parameters of an imaging machine. The system comprises a computerized device to retrieve demographic data of a person to be imaged and to generate adjustment data from the demographic data. The system further comprises an imaging machine that receives the adjustment data and adjusts certain parameters of the imaging machine in response to the adjustment data. As a result, the adjusted imaging machine is set for imaging the next person to be imaged based on that person's demographic data in an automatic manner. A user of the imaging machine is relieved from having to manually adjust the certain parameters (e.g., height position of an imaging sensor, X-ray dosage of the imaging machine).

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A method for automatically adjusting an X-ray imaging machine, said method comprising:
    using a processor-based platform to retrieve demographic data stored on a storage device worn by a next person to be imaged, wherein said demographic data includes a height, a weight, and a sex of said next person to be imaged;
    generating adjustment data based on said demographic data using said processor-based platform;
    sending said adjustment data from said processor-based platform to an X-ray imaging machine to be used to image at least a portion of said next person;
    adjusting at least one parameter of said X-ray imaging machine in response to said adjustment data; and
    imaging at least a portion of said next person with said X-ray imaging machine after adjusting said at least one parameter.

2. The method of claim 1 wherein said storage device comprises at least one of an RF ID tag and a bar code badge.

3. The method of claim 1 wherein said processor-based platform comprises at least one of a personal computer (PC), a work station, an RF ID interrogator/receiver, and a bar code scanner/reader.

4. The method of claim 1 wherein said processor-based platform in an integral part of said imaging machine.

5. The method of claim 1 wherein said adjustment data comprises position information for an imaging sensor of said imaging machine.

6. The method of claim 1 wherein said adjustment data comprises X-ray dosage information for said imaging machine.

7. The method of claim 1 wherein said X-ray imaging machine comprises an X-ray imaging sensor for taking pan-tomograph images of people.

8. The method of claim 1 wherein said X-ray imaging machine comprises a computed tomography imaging machine.

9. The method of claim 1 wherein said X-ray imaging machine includes at least one imaging sensor.

10. The method of claim 1 wherein said at least one parameter comprises a height of an imaging sensor of said X-ray imaging machine.

11. The method of claim 1 wherein said at least one parameter comprises a dosage amount to be applied by a transmitter of said X-ray imaging machine when imaging said next person and a time duration of exposure.

12. A system for automatically adjusting parameters of an X-ray imaging machine, said system comprising:
    a storage device storing demographic information of a person to be imaged, where said storage device is capable of being worn by said person to be imaged, and wherein said demographic information includes a height, a weight, and a sex of said person to be imaged;
    a computerized device capable of retrieving said demographic information from said storage device and capable of generating adjustment data based on said demographic data for said person to be imaged; and
    an X-ray imaging machine capable of receiving said adjustment data from said computerized device and capable of adjusting at least one parameter of said X-ray imaging machine in response to said adjustment data.

13. The system of claim 12 wherein said storage device comprises at least one of an RF ID tag and a bar code badge.

14. The system of claim 12 wherein said computerized device comprises at least one of a personal computer (PC), a work station, an RF ID interrogator/receiver, and a bar code scanner/reader.

15. The system of claim 12 wherein said computerized device is an integral part of said imaging machine.

16. The system of claim 12 wherein said adjustment data comprises position information for an imaging sensor of said X-ray imaging machine.

17. The system of claim 12 wherein said adjustment data comprises X-ray dosage information for said X-ray imaging machine.

18. The system of claim 12 wherein said X-ray imaging machine comprises an X-ray imaging sensor for taking pan-tomograph images of people.

19. The system of claim 12 wherein said X-ray imaging machine comprises a computed tomography imaging machine.

20. The system of claim 12 wherein said X-ray imaging machine includes at least one imaging sensor.

21. The system of claim 12 wherein said at least one parameter comprises a height of an imaging sensor of said X-ray imaging machine.

22. The system of claim 12 wherein said at least one parameter comprises a dosage amount to be applied by a transmitter of said X-ray imaging machine when imaging said at least one person.

* * * * *